US00PP07976P

United States Patent [19]

Zaiger et al.

[11] Patent Number: Plant 7,976

[45] Date of Patent: Sep. 15, 1992

[54] NECTARINE TREE "MAY KIST"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 688,677

[22] Filed: Apr. 22, 1991

[51] Int. Cl.[5] ..... A01H 5/00

[52] U.S. Cl. ..... Plt./41.1

[58] Field of Search ..... Plt./41

*Primary Examiner*—James R. Feyrer

[57] ABSTRACT

A new and distinct variety of nectarine tree with the unique combination of desirable features:

1. Early maturity of medium size fruit.
2. Heavy and regular bearer of fruit.
3. Fruit with firm flesh, good storage and shipping qualities.
4. Fruit with good flavor and eating quality.
5. Fruit with a high degree of attractive red skin color.

1 Drawing Sheet

ORIGIN OF THE VARIETY

The new variety of nectarine tree was originated by us in our experimental orchard located near Modesto, Calif., as a first generation seedling from a cross between a selected seedling, which originated from a cross between May Grand Nectarine (U.S. Plant Pat. No. 2,794) and Ruby Gold Nectarine (U.S. Plant Pat. No. 3,101), and a selection of an early maturing mutation of Arm King Nectarine (U.S. Plant Pat. No. 2,943). A large group of these first generation seedlings were grown and maintained under close observation by us, one such seedling, which is the present variety, having been especially desirable with respect to its early maturing fruit was selected for asexual reproduction and commercialization.

ASEXUAL REPRODUCTION OF THE VARIETY

The new and distinct variety of nectarine tree was asexually reproduced by budding, as performed by us in the experimental orchard located near Modesto, Calif., and shows that all characteristics of the tree and its fruit run true to form and are established and transmitted through succeeding propagations.

SUMMARY OF THE VARIETY

The new and distinct variety of nectarine tree is of large size, has vigorous upright growth, and is a heavy and productive bearer of medium sized, firm, yellow fleshed, clingstone fruit with attractive red skin color, good flavor and eating quality and has the ability to ship to long distance markets. The fruit is further characterized by early maturing and compared to May Grand Nectarine (U.S. Plant Pat. No. 2,794) and Ruby Gold Nectarine (U.S. Plant Pat. No. 3,101), the fruit matures approximately 3 weeks earlier.

PHOTOGRAPHS OF THE VARIETY

The accompanying photographs show typical specimens of the fruit and foliage of the new variety of nectarine tree, with an exterior and sectional view of the fruit shown to reveal flesh coloration and a stone remaining in place as well as the upper and lower surface of the leaves. The photographs were taken shortly after the fruit was picked at maturity (firm ripe) and the colors are as nearly true as reasonably possible in a color representation of this type.

DESCRIPTION OF THE VARIETY

The following is a detailed botanical description of the new variety of nectarine tree, its flowers, foliage and fruit, based on observations of the specimen grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Production.*—Productive.
- *Bearing.*—Regular.

Trunk:
- *Size.*—Medium to large.
- *Surface.*—Medium shaggy.
- *Color.*—Brown to grayish brown.

Branches:
- *Size.*—Medium.
- *Surface.*—Medium rough.
- *Lenticels.*—Medium number. Medium to large size.
- *Color.*—Reddish brown to brown.

Leaves:
- *Size.*—Large. Average length — 6½". Average width — 1⅝".
- *Form.*—Lanceolate. Pointed.
- *Texture.*—Smooth.
- *Thickness.*—Medium.
- *Margin.*—Crenate.
- *Petiole.*—Size — medium to short. Average length — ½". Average thickness 1/16".
- *Glands.*—Size — medium. Number varies from 1 to 5. Average number 2. Globose.
- *Color.*—Upper surface — green to dark green (27-F-6) to (27-F-7). Lower surface — green to grayish green (27-E-5) to (27-E-6).

Flower buds:
- *Size.*—Large.
- *Form.*—Plump.
- *Length.*—Medium.

Flowers:

*Size.*—Medium — non-showy.

*Blooming period.*—Date of first bloom — Feb. 28, 1990. Date of last bloom — Mar. 6, 1990. Varies slightly due to climatic conditions.

*Pollen.*—Present. Self fertile.

*Color.*—Pink.

Fruit:

*Maturity when described.*—Firm ripe.

*Date of first picking.*—May 16, 1990.

*Date of last picking.*—May 20, 1990.

*Size.*—Medium. Comparatively uniform. Average diameter axially — 2½" to 2⅝". Average transversely in suture plane — 2¼" to 2⅜".

*Form.*—Nearly Globose — slightly elongated in suture plane.

*Suture.*—Shallow — extends from base to apex.

*Ventral surface.*—Nearly rounded to very slightly lipped.

*Apex.*—Rounded to slightly retuse with slight rise in center of retuse area on some fruit.

*Base.*—Retuse.

*Cavity.*—Rounded to slightly elongated in suture plane. Average depth — ⅜". Average width — ⅝".

Flesh:

*Ripens.*—Evenly.

*Texture.*—Firm, meaty.

*Juice.*—Moderate.

*Eating quality.*—Good.

*Flavor.*—Mild — good balance between sugar and acid.

*Amygdlin.*—Undetected.

*Aroma.*—Slight.

*Fibers.*—Few; tender.

*Color.*—Pale yellow to light yellow (4-A-3) to (4-A-5).

Skin:

*Thickness.*—Medium.

*Texture.*—Tough; tenacious to flesh.

*Tendency to crack.*—Very slight.

*Down.*—Wanting.

*Color.*—Ground color; yellow to golden yellow (4-A-4) to (4-A-6). Overspread with red (9-C-8) to (9-D-8).

Stone:

*Type.*—Clingstone.

*Size.*—Medium. Average length — 1⅜". Average width — 1". Average thickness — ½".

*Form.*—Oval.

*Base.*—Straight to slightly oblique.

*Sides.*—Equal to unequal.

*Surface.*—Irregularly furrowed toward apex, somewhat pitted toward base.

*Ridges.*—Rounded.

*Tendency to split.*—Very slight.

*Color.*—Light brown to brown (7-C-5) to (7-B-5).

Use: Dessert.

*Market.*—Local and long distance.

Storage quality: Good.

Shipping quality: Good.

The present new variety of nectarine tree and its fruit herein described may vary in slight detail due to climatic, soil and cultural practices under which the variety may be grown; the present description is that of the new variety grown under the ecological condition prevailing near Modesto, Calif.

We claim:

1. A new and distinct variety of nectarine tree substantially as illustrated and described, characterized by large size, vigorous upright growth; it is a productive and regular bearer of medium size, firm, clingstone fruit with good eating, storage and shipping qualities; the early maturing fruit is further characterized in comparison to the May Grand Nectarine (U.S. Plant Pat. No. 2,794) and the Ruby Gold Nectarine (U.S. Plant Pat. No. 3,101) by its maturing approximately 3 weeks earlier.

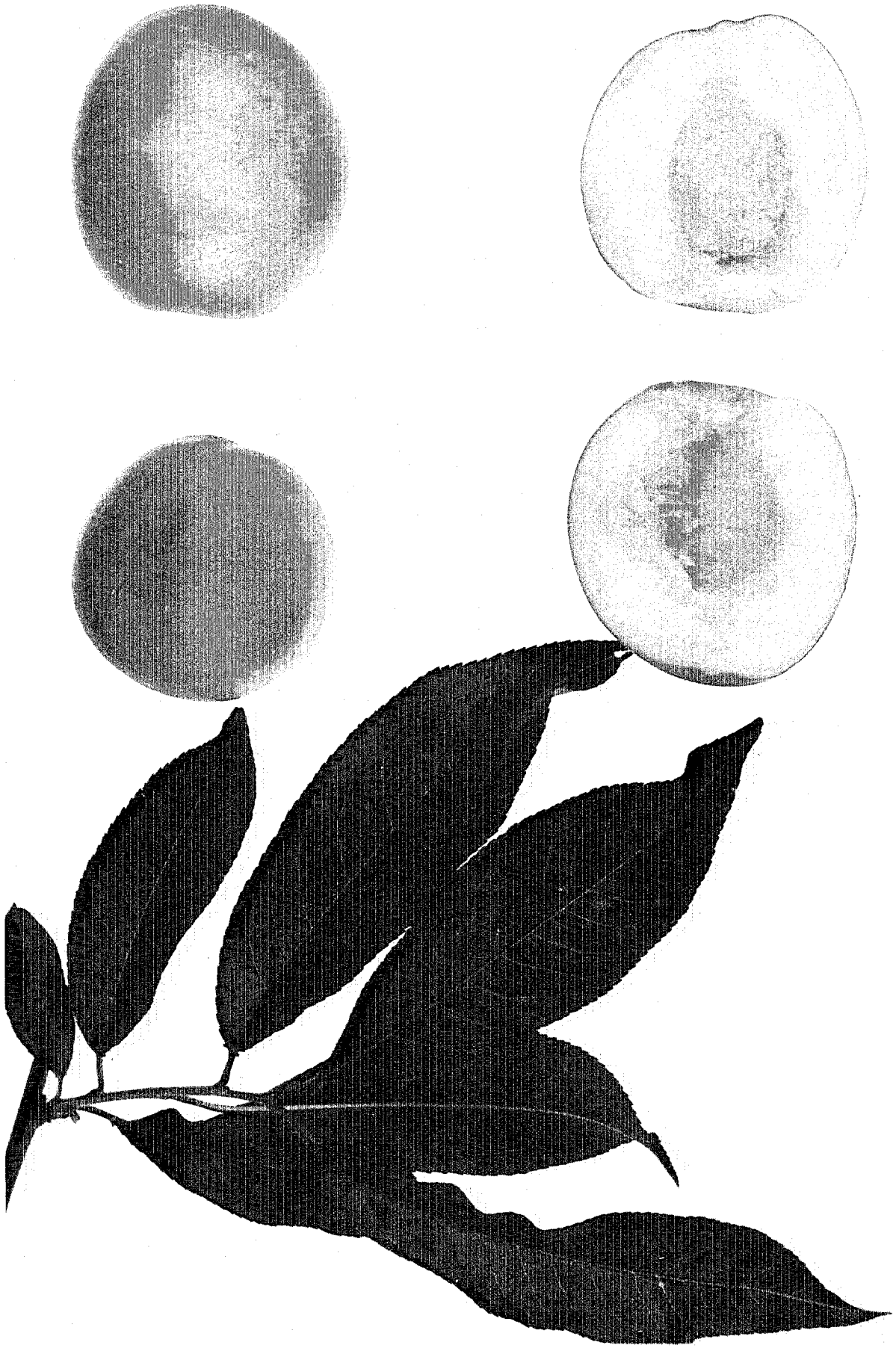

* * * * *